US012705733B2

(12) United States Patent
Park et al.

(10) Patent No.: US 12,705,733 B2
(45) Date of Patent: Aug. 11, 2026

(54) METHOD AND APPARATUS FOR TUMOR PURITY BASED ON PATHOLOGICAL SLIDE IMAGE

(71) Applicant: LUNIT INC., Seoul (KR)

(72) Inventors: Ga Hee Park, Seoul (KR); Chan Young Ock, Seoul (KR); Kyung Hyun Paeng, Seoul (KR)

(73) Assignee: LUNIT INC., Seoul (KR)

(*) Notice: Subject to any disclaimer, the term of this patent is extended or adjusted under 35 U.S.C. 154(b) by 742 days.

(21) Appl. No.: 17/703,484

(22) Filed: Mar. 24, 2022

(65) Prior Publication Data

US 2023/0206432 A1 Jun. 29, 2023

(30) Foreign Application Priority Data

Dec. 28, 2021 (KR) ........................ 10-2021-0190443
Feb. 21, 2022 (KR) ........................ 10-2022-0022290

(51) Int. Cl.
*G06T 7/00* (2017.01)
*G16H 30/20* (2018.01)
(Continued)

(52) U.S. Cl.
CPC ........... *G06T 7/0012* (2013.01); *G16H 30/20* (2018.01); *G16H 30/40* (2018.01); *G06T 2207/30096* (2013.01); *G16H 50/20* (2018.01)

(58) Field of Classification Search
CPC ......... G06T 7/0012; G06T 2207/30096; G06T 2207/10056; G06T 2207/30024; G06T 2207/20084; G06T 7/11; G06T 2207/20081; G06T 7/62; G06T 2207/30242; G16H 30/20; G16H 30/40;
(Continued)

(56) References Cited

U.S. PATENT DOCUMENTS 8,165,363 B2 4/2012 Soenksen et al.
8,705,825 B2 4/2014 Olson et al.
(Continued)

FOREIGN PATENT DOCUMENTS

EP 3 593 357 A0 1/2020
EP 3936870 A2 * 1/2022 ........... G01N 1/4044
(Continued)

OTHER PUBLICATIONS

Justia, "Systems and methods for processing electronic images for biomarker localization", Paige.AI, Inc., Jan. 27, 2021, 12pgs.
(Continued)

*Primary Examiner* — Xuemei G Chen
(74) *Attorney, Agent, or Firm* — Sughrue Mion, PLLC

(57) ABSTRACT

Provided is a computing apparatus including: at least one memory; and at least one processor, wherein the at least one processor is configured to: perform a first classification on a plurality of tissues expressed in a pathological slide image by analyzing the pathological slide image, perform a second classification on a plurality of cells expressed in a pathological slide image by analyzing the pathological slide image, and calculate tumor purity including information on noise included in the pathological slide image by combining a first classification result and a second classification result.

18 Claims, 12 Drawing Sheets

(51) Int. Cl.
*G16H 30/40* (2018.01)
*G16H 50/20* (2018.01)

(58) Field of Classification Search
CPC ........ G16H 50/20; G16H 50/70; G16H 50/30; G06V 20/698; G06V 10/764; G06V 10/82; G06V 20/69; G06V 2201/03; G06V 20/695; G06N 3/045; G16B 20/00; G16B 5/00; G16B 40/00; C12Q 1/6886
See application file for complete search history.

(56) References Cited

U.S. PATENT DOCUMENTS

| | | | | |
|---|---|---|---|---|
| 9,355,445 | B2 | 5/2016 | Yamashita et al. | |
| 10,977,791 | B2 * | 4/2021 | Chukka | G06V 20/695 |
| 2011/0189670 | A1 * | 8/2011 | Katz | C12Q 1/6886 435/6.11 |
| 2012/0082365 | A1 * | 4/2012 | Yoshihara | G06K 9/00 382/133 |
| 2015/0003716 | A1 | 1/2015 | Lloyd et al. | |
| 2016/0063724 | A1 | 3/2016 | Tunstall et al. | |
| 2016/0110584 | A1 * | 4/2016 | Remiszewski | G06K 9/00 |
| 2017/0046839 | A1 | 2/2017 | Paik et al. | |
| 2017/0138941 | A1 * | 5/2017 | Cao | G01N 33/587 |
| 2017/0270666 | A1 | 9/2017 | Barnes et al. | |
| 2018/0046759 | A1 * | 2/2018 | Barral | G06F 19/00 |
| 2019/0236780 | A1 | 8/2019 | Barnes et al. | |
| 2020/0149097 | A1 | 5/2020 | Otto et al. | |
| 2020/0152316 | A1 * | 5/2020 | Lee | G16H 50/20 |
| 2020/0160032 | A1 * | 5/2020 | Allen | G06N 3/045 |
| 2020/0211189 | A1 * | 7/2020 | Yip | G06T 7/0012 |
| 2020/0279354 | A1 * | 9/2020 | Klaiman | G06N 3/0455 |
| 2020/0291457 | A1 | 9/2020 | Blauwkamp et al. | |
| 2020/0321102 | A1 * | 10/2020 | Barnes | G16H 30/40 |
| 2020/0365268 | A1 * | 11/2020 | Michuda | G16H 50/20 |
| 2020/0381121 | A1 * | 12/2020 | Wang | G16H 50/20 |
| 2021/0018742 | A1 | 1/2021 | Stumpe | |
| 2021/0133966 | A1 * | 5/2021 | Fuchs | G06N 3/045 |
| 2021/0166380 | A1 * | 6/2021 | Yip | G06N 3/045 |
| 2021/0166381 | A1 | 6/2021 | Yip et al. | |
| 2021/0166785 | A1 * | 6/2021 | Yip | G06V 10/44 |
| 2021/0183524 | A1 * | 6/2021 | Lee | G16B 50/10 |
| 2021/0256690 | A1 * | 8/2021 | Yip | G06T 1/20 |
| 2021/0388418 | A1 | 12/2021 | Skanderup et al. | |
| 2022/0025443 | A1 | 1/2022 | Korani et al. | |
| 2022/0036971 | A1 * | 2/2022 | Yoo | G16B 20/00 |
| 2022/0154295 | A1 * | 5/2022 | Velculescu | A61K 39/3955 |
| 2022/0195419 | A1 | 6/2022 | Jaimovich et al. | |
| 2022/0221460 | A1 * | 7/2022 | Kim | G01N 1/4044 |
| 2022/0270244 | A1 * | 8/2022 | Chuang | G06N 3/08 |
| 2023/0407404 | A1 * | 12/2023 | Baumgartner | C12Q 1/6886 |
| 2024/0169530 | A1 * | 5/2024 | Ichinoo | G01N 21/6486 |
| 2024/0361245 | A1 * | 10/2024 | Yasukawa | G01N 15/1433 |

FOREIGN PATENT DOCUMENTS

| | | | | |
|---|---|---|---|---|
| KR | 10-2021-0136571 | A | 11/2021 | |
| WO | WO-2004019264 | A1 * | 3/2004 | G06K 9/62 |
| WO | WO-2007061469 | A1 * | 5/2007 | A61B 5/00 |
| WO | 2016/087592 | A1 | 6/2016 | |
| WO | 2017/087415 | A1 | 5/2017 | |
| WO | WO-2019136234 | A1 * | 7/2019 | G01N 27/62 |
| WO | WO-2020193651 | A1 * | 10/2020 | G06T 7/00 |
| WO | 2021/052310 | A1 | 3/2021 | |

OTHER PUBLICATIONS

Justia, “Systems and methods for processing electronic images to detect contamination”, Paige.AI, Inc., Dec. 11, 2020, 35 pgs.
“Systems and methods for processing images to classify the processed images for digital pathology”. paige.ai, Inc., Dec. 4, 2020, 10 pgs.
“Systems and Methods to Process Electronic Images to Determine Salient Information in Digital Pathology”, paige.ai, Inc., May 6, 2021, 7 pgs.
Matthew Brendel et al., “Weakly-Supervised Tumor Purity Prediction From Frozen H&E Stained Slides”, Nov. 11, 2021, 22 pgs., bioRxiv preprint doi: https://doi.org/10.1101/2021.11.09.467901.
Communication dated May 25, 2023 issued by the European Patent Office in application No. 22206669.8.
Lee AD Cooper, et al., “Novel genotype-phenotype associations in human cancers enabled by advanced molecular platforms and computational analysis of whole slide images”, Pathobiology in Focus, Apr. 2015, vol. 95., pp. 366-376.
Communication dated Aug. 4, 2023 issued by the Korean Patent Office in application No. 10-2022-0071642.
Henrik Failmezger, et al., “Topological Tumor Graphs: A Graph-Based Spatial Model to Infer Stromal Recruitment for Immunosuppression in Melanoma Histology”, Cancer Research, vol. 80, No. 5, Mar. 1, 2020, pp. 1199-1209.
Minho Cho, et al., “Tissue recommendations for precision cancer therapy using next generation sequencing: a comprehensive single cancer center’s experiences”, Oncotarget, 2017, vol. 8, No. 26, pp. 42478-42486.
Samantha N. McNulty, et al., “Impact of Reducing DNA Input on Next-Generation Sequencing Library Complexity and Variant Detection”, The Journal of Molecular Diagnostics, vol. 22, No. 5, May 2020, pp. 720-727.
Communication dated Feb. 27, 2023 issued by the Korean Patent Office in application No. 10-2022-0071642.
International Search Report (PCT/ISA/210) dated Sep. 19, 2022 issued by the International Searching Authority in International Application No. PCT/KR2022/004054.

* cited by examiner

FIG. 8

| Tumor purity | |
|---|---|
| AI-P (%) | 0.35 |
| CEA (%) | 25.33 |
| Expected biological noise (%) from cancer area | 20.09 |
| Technical noise (%) | 1.96 |
| Non-Cancer region (%) from a slide | 60.08 |
| Single cell DNA weight (gram) | 6.E-12 |
| Total cell count | 2372573.00 |
| Expected DNA yield from a slide (ng) | 14235.44 |
| Expected tumor DNA yield from a slide (ng) | 49.75 |

810

820

METHOD AND APPARATUS FOR TUMOR PURITY BASED ON PATHOLOGICAL SLIDE IMAGE

CROSS-REFERENCE TO RELATED APPLICATION

This application is based on and claims priority under 35 USC § 119 to Korean Patent Applications Nos. 10-2021-0190443, filed on Dec. 28, 2021, and 10-2022-0022290, filed on Feb. 21, 2022, in the Korean Intellectual Property Office, the disclosure of which is incorporated by reference herein in its entirety.

BACKGROUND

1. Field

The present disclosure relates to a method and apparatus for predicting tumor purity based on pathological slide images.

2. Description of the Related Art

The field of digital pathology is the field of obtaining histological information or predicting a prognosis of a patient by using a whole slide image generated by scanning a pathological slide image.

The pathology slide image may be obtained from a stained tissue sample of the subject. For example, tissue samples can be stained by various staining methods such as hematoxylin and eosin, trichrome, periodic acid schiff, autoradiography, enzyme histochemistry, immuno-fluorescence, and immunohistochemistry. Since stained tissue samples are used for the histological and biopsy evaluations, they can be used as a basis on deciding whether to move on to molecular profile analysis to understand the disease state.

However, the conventional calculation of tumor purity using pathological slide image analysis has a limitation in that various biological noise and technical noise affecting reduced nucleic acid quality, fragmentation, and deamination of cytosine bases are not taken into consideration.

SUMMARY

One or more embodiments include a method and apparatus for predicting tumor purity based on a pathological slide image. One or more embodiments include a computer-readable recording medium having recorded thereon a program for executing the method in a computer. The technical objectives to be solved are not limited to the technical problems as described above, and other technical objectives may exist.

Additional aspects will be set forth in part in the description which follows and, in part, will be apparent from the description, or may be learned by practice of the presented embodiments of the disclosure.

An aspect provides a computing apparatus including: at least one memory; and at least one processor, wherein the at least one processor is configured to: perform a first classification on a plurality of tissues expressed in a pathological slide image by analyzing the pathological slide image, perform a second classification on a plurality of cells expressed in a pathological slide image by analyzing the pathological slide image, and calculate tumor purity including information on noise included in the pathological slide image by combining a first classification result and a second classification result.

Another aspect provides a method of interpreting a pathological slide image, the method including: performing a first classification on a plurality of tissues expressed in the pathological slide image by analyzing the pathological slide image; performing a second classification on a plurality of cells expressed in a pathological slide image by analyzing the pathological slide image, and calculating tumor purity including information on noise included in the pathological slide image by combining a first classification result and a second classification result.

A computer-readable recording medium according to another aspect includes a recording medium recording the method for executing the above-described method in a computer.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 8 shows a view for describing an example in which tumor purity and at least one index are output according to an embodiment;

DETAILED DESCRIPTION

Figure 1:
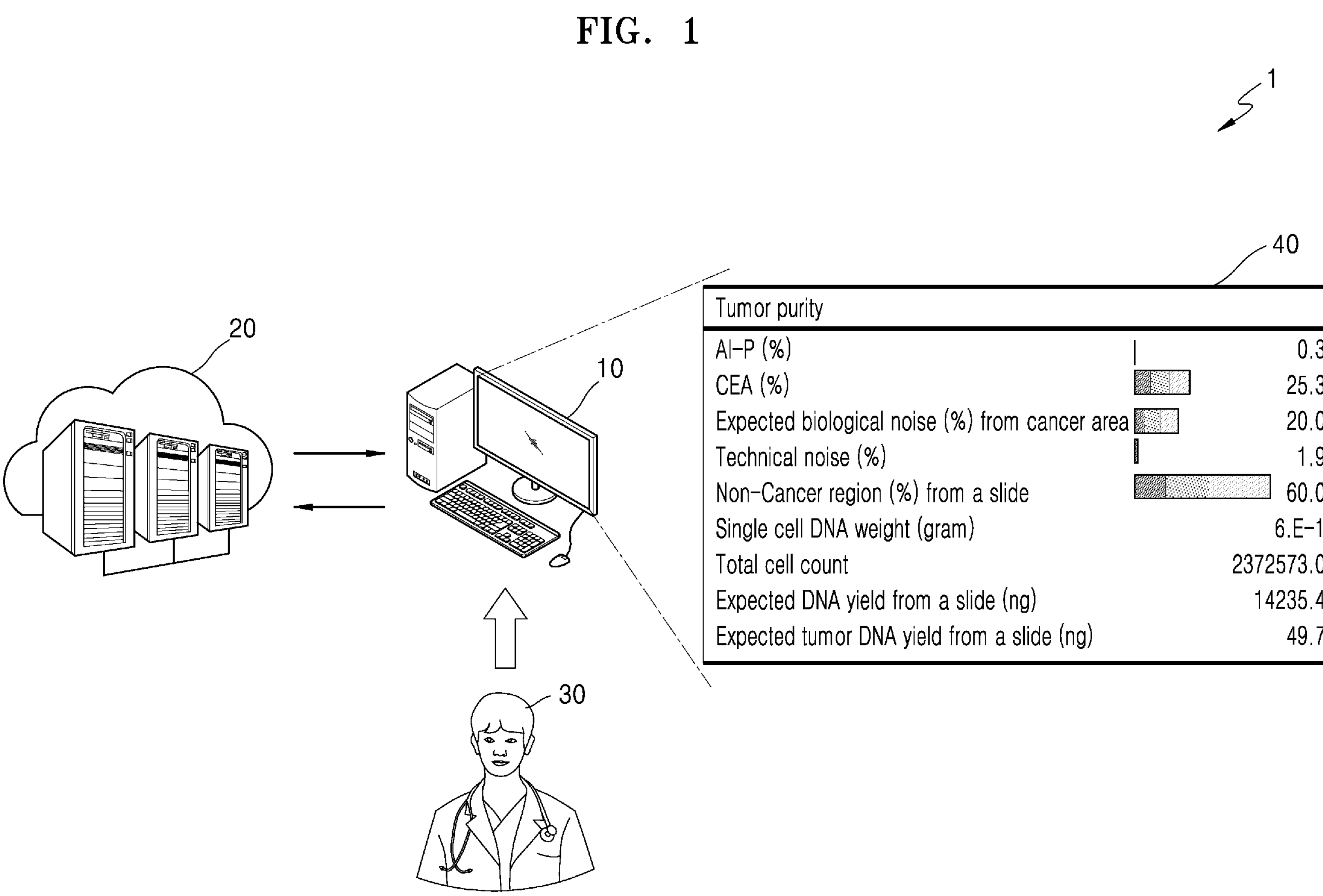
FIG. 1 shows a diagram for describing an example of a system for analyzing a pathological slide image according to an embodiment.

As terms used in embodiments provided herein, general terms that are currently widely used are selected. However, these terms may be understood as having different meanings depending on the intention or precedent of a person skilled in the art, the emergence of new technology, and the like. In addition, in a specific case, there is a term arbitrarily selected by the applicant, and in this case, the meaning will be described in detail in the corresponding description. Therefore, the terms used in the specification should be defined based on the meaning of the term and the content provided throughout the entire specification, rather than the simple name of the term.

In the entire specification, when a part "includes" a certain element, it means that other elements may be further included, rather than excluding other elements, unless stated otherwise. In addition, the terms " . . . unit" and " . . . module" refer to a unit that processes at least one function or operation, which may be implemented as hardware or software, or a combination of hardware and software.

Also, terms including an ordinal number such as "first" or "second" used in the specification may be used to describe various elements, but the elements should not be limited by the terms. The terms may be used for the purpose of distinguishing one component from another component.

According to an embodiment, the term 'pathological slide image' may refer to an image obtained by photographing a pathological slide of, for example, a tissue removed from the human body after being fixed and stained through a series of chemical treatment processes. In addition, the pathological slide image may refer to a whole slide image (WSI) including a high-resolution image of the entire slide, and may refer to a part of the entire slide image, for example, one or more patches. For example, a pathological slide image may refer to a digital image taken or scanned by a scanning device (e.g., a digital scanner, etc.), and may include information about a specific protein, cell, tissue, and/or structure. In addition, the pathological image may include one or more patches, and histological information may be applied (e.g., tagged) to the one or more patches through an annotation operation.

According to an embodiment, 'medical information' may refer to any medically meaningful information that can be extracted from a medical image, for example, the area, location, and size of a tumor cell in the medical image, diagnostic information about cancer, information associated with a patient's likelihood of developing cancer, and/or a medical conclusion associated with cancer treatment. However, embodiments of the present disclosure are not limited thereto. In addition, the medical information may include not only quantified numerical values obtainable from a medical image, but also information obtained by visualizing numerical values, prediction information according to numerical values, image information, statistical information, and the like. The generated medical information may be provided to a user terminal or output or transmitted to a display device and displayed.

Hereinafter, an embodiment will be described in detail with reference to the accompanying drawings. However, the embodiment may be implemented in several different forms and is not limited to the examples described herein.

FIG. 1 shows a diagram for describing an example of a system 1 for analyzing a pathological slide image according to an embodiment.

Referring to FIG. 1, the system 1 includes a user terminal 10 and a server 20. For example, the user terminal 10 and the server 20 may be connected through a wired or wireless communication method to transmit/receive data (e.g., image data, etc.) therebetween.

For convenience of description, although FIG. 1 illustrates that the system 1 includes the user terminal 10 and the server 20, the system 1 is not limited thereto. For example, the system 1 may include other external devices (not shown), and operations of the user terminal 10 and the server 20 to be described below may be performed by a single device (e.g., the user terminal 10) or many devices.

The user terminal 10 may be a computing apparatus including a display device, a device for receiving a user input (e.g., a keyboard, a mouse, etc.), and including a memory and a processor. For example, the user terminal 10 may be a notebook PC, a desktop PC, a laptop, a tablet computer, a smart phone, or the like, but is not limited thereto.

The server 20 may be a device that communicates with an external device (not shown) including the user terminal 10 shown in FIG. 1. In an embodiment, the server 20 may be a device for storing various data including pathological slide images and information on tumor purity. In an embodiment, the server 20 may be a computing apparatus including a memory and a processor and having its own computational capability. When the server 20 is a computing apparatus, the server 20 may perform at least some of the operations of the user terminal 10 to be described later with reference to FIGS. 1 to 11. For example, the server 20 may be a cloud server, but is not limited thereto.

The user terminal 10 may output a pathological slide image and/or tumor purity information 40. In this regard, the tumor purity information 40 may include numerical values derived by the user terminal 10 interpreting the pathological slide image.

The pathological slide image may refer to an image of a pathological slide of, for example, the tissue removed from the human body and fixed and stained through a series of chemical treatment processes in order to identify the same through a microscope. In an embodiment, the pathological slide image may refer to a whole slide image including a high-resolution image of the entire slide. In an embodiment, the pathological slide image may refer to a portion of the entire slide image of such high resolution.

On the other hand, the pathological slide image may refer to a patch area obtained by dividing the entire slide image in a patch unit. For example, a patch may have a size of a certain area. In an embodiment, the patch may refer to an area including each of the included objects in the entire slide.

In addition, the pathological slide image may refer to a digital image obtained using a microscope, and may include information on cells, tissues, and/or structures in the human body.

The tumor purity information 40 may include not only information on cancer areas and tumor cells expressed in the pathological slide image, but also information on areas and cells which are not related to tumors. In the present disclosure, information about areas and cells that are not related to a tumor, may be referred to as unnecessary noise to determine a disease state. For example, a noise may include at least one of a biological noise (e.g., a normal area of a pathological slide image, etc.) and a technical noise (e.g., a degraded area, etc.) included in the pathological slide image. However, the type of noise is not limited thereto. In other words, any area that corresponds to an area and a cell which are not related to a tumor in the pathological slide image, may correspond to noise without limitation.

Conventionally, in calculating the tumor purity, attention was paid only to the cancer area and tumor cells in the pathological slide image. Specifically, in the prior art, tumor purity was calculated for tissues or cells stained with a specific pattern in a pathological slide image. Accordingly, the prior art has a limitation that various noise affecting degraded nucleic acid quality, fragmentation, deamination of cytosine bases, etc. are not considered, and may not provide the user 30 with accurate information on the tumor purity. That is, according to the information on tumor purity according to the prior art, the likelihood of being determined as false negative or false positive is high.

The system 1 according to an embodiment generates the tumor purity information 40 in consideration of noise as well as a cancer region and a tumor cell in the pathological slide image. In an embodiment, the user terminal 10 analyzes the pathological slide image to perform a first classification on a plurality of tissues expressed in the pathological slide image, and analyzes the pathological slide image to perform a second classification on a plurality of cells expressed in the pathological slide image. Then, the user terminal 10 calculates the tumor purity including information on noise included in the pathological slide image by combining the first classification result and the second classification result. Accordingly, a user 30 may identify accurate information on tumor purity for tissues and cells expressed in the pathological slide image.

The user terminal 10 according to an embodiment calculates the tumor purity for all cancer types of The Cancer Genome Atlas (TCGA). Specifically, the user terminal 10 may use an AI model trained to predict 32 types of tumor samples of TCGA. Therefore, based on the information on the tumor purity calculated by the user terminal 10 according to an embodiment, the user 30 may accurately diagnose all types of cancer.

Also, the user terminal 10 according to an embodiment may calculate an index indicating an expected cancer signal. In this regard, the index indicating the expected cancer signal may include at least one of an expected DNA yield for all cells and an expected tumor DNA yield for tumor cells. Accordingly, the user 30 may determine whether to perform an additional experiment to diagnose the disease.

Hereinafter, examples in which the user terminal 10 interprets a pathological slide image to calculate tumor purity or at least one index indicating an expected cancer signal will be described.

Meanwhile, for convenience of explanation, it has been described throughout the specification that the user terminal 10 interprets the pathological slide image to calculate the tumor purity or calculates at least one index indicating the expected cancer signal, but embodiments of the present disclosure are not limited thereto. For example, at least some of the operations performed by the user terminal 10 may be performed by the server 20.

In other words, at least some of the operations of the user terminal 10 described with reference to FIGS. 1 to 11 may be performed by the server 20. For example, the server 20 may interpret the pathological slide image to calculate tumor purity or calculate at least one index indicating an expected cancer signal, and transmit the calculation result to the user terminal 10. Then, the user terminal 10 may output the information transmitted by the server 20 (e.g., a pathological slide image, information on tumor purity, an index indicating an expected cancer signal, etc.), or provide medical information generated by processing the transmitted information. However, the operation of the server 20 is not limited thereto.

Figure 2A:
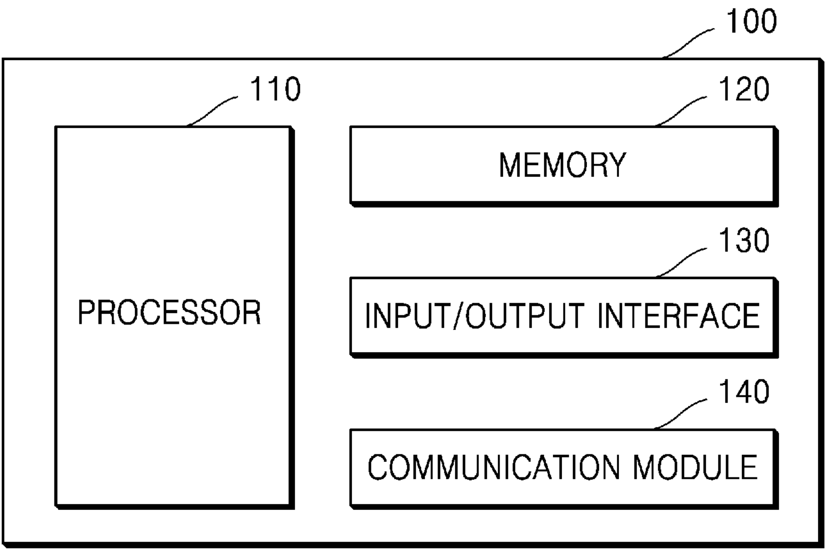
FIG. 2A shows a block diagram illustrating an example of a user terminal according to an embodiment.

FIG. 2A shows a block diagram illustrating an example of a user terminal according to an embodiment.

Referring to FIG. 2A, the user terminal 100 includes a processor 110, a memory 120, an input/output interface 130, and a communication module 140. For convenience of explanation, only components related to the present disclosure are illustrated in FIG. 2A. Accordingly, other general-purpose components than the components illustrated in FIG. 2A may be further included in the user terminal 100. In addition, the processor 110, the memory 120, the input/output interface 130, and the communication module 140 illustrated in FIG. 2A may be implemented as independent devices, which is obvious to one of ordinary skill in the art related to the present disclosure.

The processor 110 may process a command of a computer program by performing basic arithmetic, logic, and input/output calculations. In this regard, the command may be provided from the memory 120 or an external device (e.g., the server 20, etc.). In addition, the processor 110 may control overall operations of other components included in the user terminal 100.

In an embodiment, the processor 110 interprets the pathological slide image to calculate tumor purity. In an embodiment, the processor 110 analyzes the pathological slide image and performs a first classification on a plurality of tissues expressed in the pathological slide image. Then, the processor 110 analyzes the pathological slide image and performs a second classification on the plurality of cells expressed in the pathological slide image. Then, the processor 110 calculates tumor purity including information on noise included in the pathological slide image by combining the first classification result and the second classification result.

In addition, the processor 110 interprets the pathological slide image to calculate at least one index representing the expected cancer signal. In this regard, the processor 110 may calculate at least one of an expected DNA yield for all cells and an expected tumor DNA yield for tumor cells.

In addition, the processor 110 controls the display device to output tumor purity and an index indicating an expected cancer signal. In addition, the processor 110 compares the index indicating the expected cancer signal with a preset threshold to provide a guide on whether to perform an additional experiment.

Specific examples in which the processor 110 according to an embodiment operates will be described with reference to FIGS. 3 to 11.

The processor 110 may be implemented as an array of a plurality of logic gates, or may be implemented as a combination of a general-purpose microprocessor and a memory in which a program executable in the microprocessor is stored. For example, the processor 110 may include a general-purpose processor, a central processing unit (CPU), a microprocessor, a digital signal processor (DSP), a controller, a microcontroller, a state machine, and the like. In some circumstances, the processor 110 may include an application-specific integrated circuit (ASIC), a programmable logic device (PLD), a field programmable gate array (FPGA), or the like. For example, the processor 110 may refer to a combination of processing devices, such as a combination of a digital signal processor (DSP) and a microprocessor, a combination of a plurality of microprocessors, a combination of one or more microprocessors coupled with a digital signal processor (DSP) core, or a combination of any other configurations.

The memory 120 may include any non-transitory computer-readable recording medium. In an embodiment, the memory 120 may include a permanent mass storage device such as a random access memory (RAM), a read only memory (ROM), a disk drive, a solid state drive (SSD), a flash memory, etc. device). In an embodiment, a permanent mass storage device such as a ROM, SSD, a flash memory, a disk drive, etc. may be a separate permanent storage device which is distinguishable from the memory. In addition, an operating system (OS) and at least one program code (e.g., a code for the processor 110 to perform an operation to be described later with reference to FIGS. 3 to 11) may be stored in the memory 120.

These software components may be loaded from a computer-readable recording medium separate from the memory 120. The separate computer-readable recording medium may be a recording medium that may be directly connected to the user terminal 100, for example, a computer-readable recording medium, such as a floppy drive, a disk, a tape, a DVD/CD-ROM drive, a memory card, or the like. In an embodiment, the software components may be loaded into the memory 120 through the communication module 140 instead of a computer-readable recording medium. For example, at least one program may be loaded into the memory 120 based on a computer program (for example, a computer program for performing, by the processor 110, an operation to be described later with reference to FIGS. 3 to 11) installed by the files provided through the communication module 140 by developers or a computer file distribution system that distributes the installation files of applications.

The input/output interface 130 may be a member for an interface with a device (e.g., a keyboard, a mouse, etc.) for input or output, the member being connected to the user terminal 100 or being included in the user terminal 100. In FIG. 2, the input/output interface 130 is illustrated as an element configured separately from the processor 110, but the present disclosure is not limited thereto, and the input/output interface 130 may be configured to be included in the processor 110.

The communication module 140 may provide a configuration or function for the server 20 and the user terminal 100 to communicate with each other through a network. In addition, the communication module 140 may provide a configuration or function for the user terminal 100 to communicate with another external device. For example, a control signal, a command, data, etc. provided according to the control of the processor 110, may be transmitted to the server 20 and/or an external device through the communication module 140 and the network.

Meanwhile, although not illustrated in FIG. 2A, the user terminal 100 may further include a display device. In an embodiment, the user terminal 100 may be connected to an independent display device through a wired or wireless communication method to transmit/receive data to or from each other.

For example, through the display device, a pathological slide image, a value calculated through interpretation of the pathological slide image (e.g., tumor purity, an index indicating an expected cancer signal, etc.), medical information generated from the calculated value, etc. may be provided to the user 30.

Figure 2B:
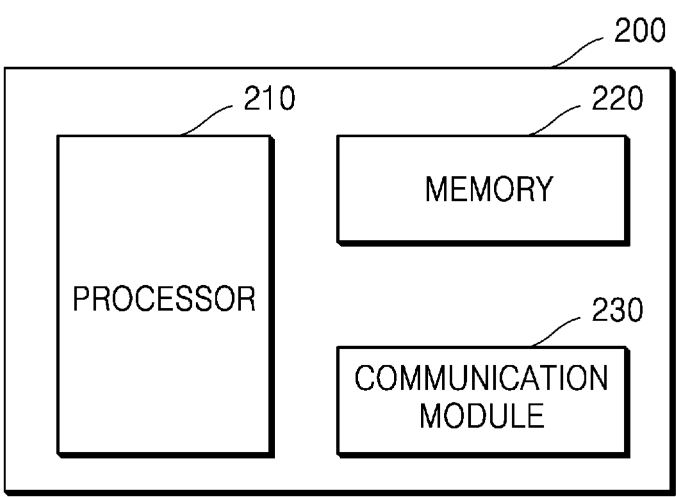
FIG. 2B shows a block diagram illustrating an example of a server according to an embodiment.

FIG. 2B shows a block diagram illustrating an example of a server 200 according to an embodiment.

Referring to FIG. 2B, the server 200 includes a processor 210, a memory 220, and a communication module 230. For convenience of explanation, only components related to the present disclosure are illustrated in FIG. 2B. Accordingly, other general-purpose components other than the components illustrated in FIG. 2B may be further included in the server 200. In addition, the processor 210, the memory 220, and the communication module 230 illustrated in FIG. 2B may be implemented as independent devices, which is obvious to one of ordinary skill in the art related to the present disclosure.

The processor 210 may obtain a pathological slide image from at least one of the memory 220, which is an internal memory, an external memory (not shown), the user terminal 10, or an external device. The processor 210 interprets the pathological slide image to calculate tumor purity and/or at least one index indicating an expected cancer signal. In other words, the operation of the processor 110 described above with reference to FIG. 2A may be performed by the processor 210. In this case, the user terminal 10 may output information transmitted by the server 200 through a display device.

Meanwhile, since an example of the processor 210 is the same as the example of the processor 110 described above with reference to FIG. 2A, a detailed description thereof will be omitted.

A pathological slide image and various data such as data generated according to an operation of the processor 210, may be stored in the memory 220. In an embodiment, an operating system (OS) and at least one program (e.g., a program necessary for the operation of the processor 210, etc.), may be stored in the memory 220.

Meanwhile, since an example of the memory 220 is the same as the example of the memory 210 described above with reference to FIG. 2A, a detailed description thereof will be omitted.

The communication module 230 may provide a configuration or function for the server 200 and the user terminal 100 to communicate with each other through a network. In addition, the communication module 230 may provide a configuration or function for the server 200 to communicate with another external device. For example, a control signal, a command, data, etc. provided according to the control of the processor 210, may be transmitted to the user terminal 100 and/or an external device through the communication module 230 and the network.

Figure 3:
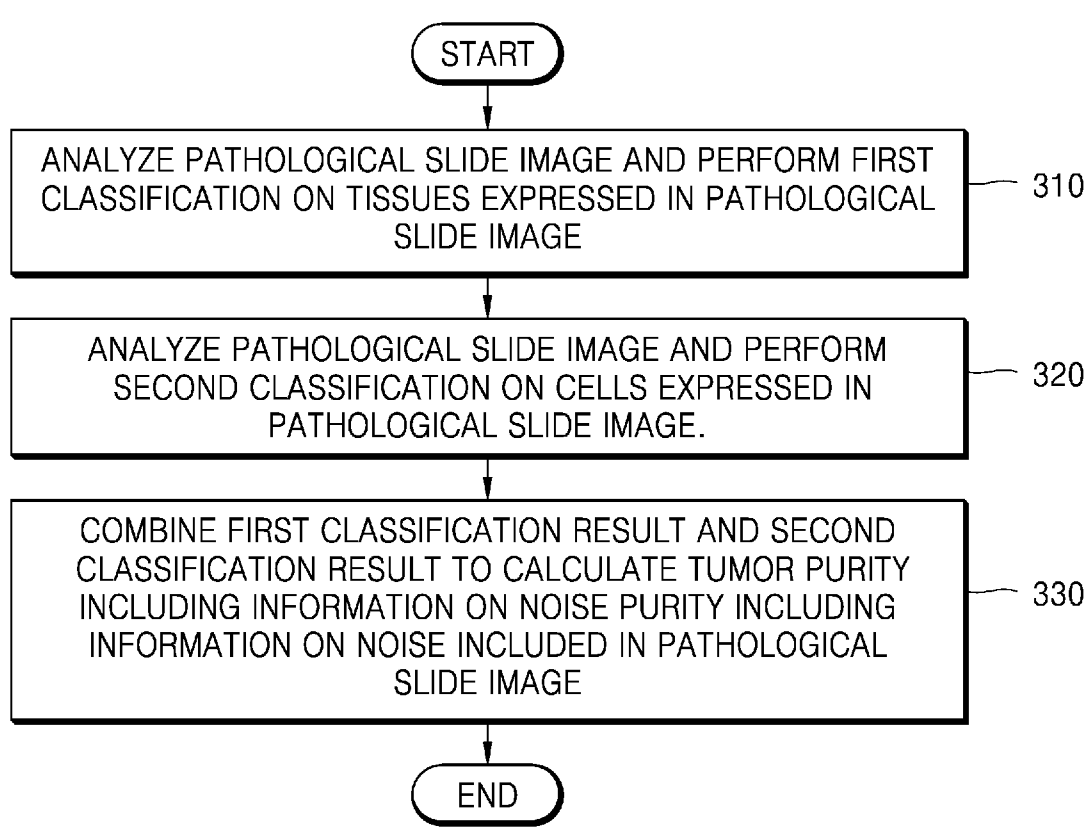
FIG. 3 shows a flowchart illustrating an example of a method of interpreting a pathological slide image according to an embodiment.

FIG. 3 shows a flowchart illustrating an example of a method of interpreting a pathological slide image according to an embodiment.

Referring to FIG. 3, a method of outputting a pathological slide image includes operations that are time-series processed by the user terminals 10 and 100 or the processor 110 illustrated in FIGS. 1 and 2. Therefore, the descriptions provided above with respect to the user terminals 10 and 100 or the processor 110 illustrated in FIGS. 1 and 2 may also be applied to the method of outputting the pathological slide image of FIG, even when those are omitted herein.

In operation 310, the processor 110 analyzes the pathological slide image and performs a first classification on a plurality of tissues expressed in the pathological slide image. The pathological slide image may be obtained from at least one of the memory 120, which is an internal memory, an external memory (not shown), a server 200, or an external input/output device.

First, the processor 110 analyzes a pathological slide image. In an embodiment, by analyzing the pathological slide image using a predetermined image processing technique, the processor 110 may detect areas corresponding to tissues from the pathological slide image, and may separate layers representing the tissues. In an embodiment, by using a machine learning model, the processor 110 may detect areas corresponding to tissues from the pathological slide image and separate layers representing tissues. In this case, by using learning data including a plurality of reference pathological slide images and a plurality of reference label information, the machine learning model may be trained to detect regions corresponding to tissues in the reference pathological slide images, and separate layers representing the tissues.

The processor 110 performs a first classification on the plurality of tissues expressed in the pathological slide image. In an embodiment, the processor 110 may classify the pathological slide image into at least one of a cancer area, a cancer stroma area, a necrosis area, and a background area. In this regard, the background area may include an area representing biological noise and/or an area representing technical noise. For example, an area representing a biological noise may include a normal area, and an area representing a technical noise may include a degraded area.

However, an example in which the processor 110 classifies the pathological slide image into at least one an area expressed in the pathological slide image, is not limited to the above-described example. In other words, without being limited to the four types of areas (the cancer area, the cancer stroma area, the necrosis area, and the background area), the processor 110 may classify at least one area expressed in the pathological slide image according to various criteria, into a plurality of categories. At least one region expressed in the pathological slide image may be classified into a plurality of categories according to a preset criterion or a criterion set by a user. The types of noise are not limited to biological noise and technical noise, as described above with reference to FIG. 1.

Hereinafter, an example in which the processor 110 performs a first classification on a plurality of organizations, will be described with reference to FIG. 4.

Figure 4:
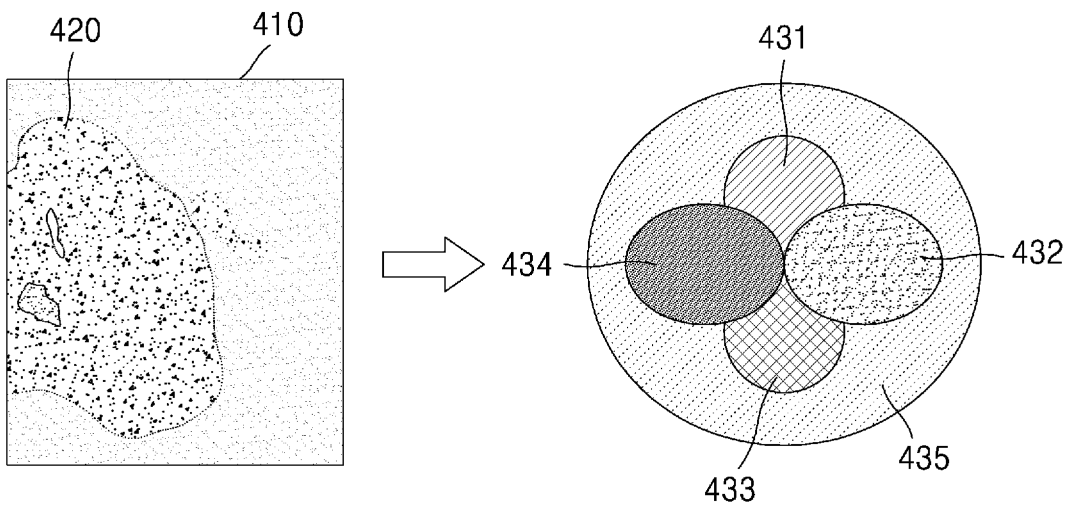
FIG. 4 shows a diagram for describing an embodiment in which a processor performs a first classification on a plurality of tissues according to an embodiment.

FIG. 4 shows a diagram for describing an embodiment in which a processor performs a first classification on a plurality of tissues according to an embodiment.

Referring to FIG. 4, the processor 110 analyzes a pathological slide image 410 to detect an area representing a tissue 420, and separates a layer representing the tissue 420. The tissue 420 of the pathological slide image 410 may include areas 431 to 435, and the processor 110 classifies the areas 431 to 435. In an embodiment, the areas 431 to 435 classified by the processor 110 may include a cancer area 431, a cancer stroma area 432, a necrosis area 433, a degraded area 434, and a normal area 435.

As described above with reference to FIG. 1, the processor 110 identifies the degraded area 434 and the normal area 435, which correspond to noise, in the pathological slide image 410, and calculates the tumor purity in consideration of the degraded area 434 and the normal area 435. Therefore, as compared to the prior art, accurate information on tumor purity may be delivered to the user 30. Accordingly, the user 30 can accurately perform the diagnosis of a disease based on the pathological slide image 410 or the deciding whether there is a need for additional experiments.

Referring to FIG. 3, in operation 310, the processor 110 analyzes the pathological slide image and performs a second classification on a plurality of cells expressed in the pathological slide image.

First, the processor 110 analyzes the pathological slide image, detects cells from the pathological slide image, and separates layers representing the cells. A specific method for the processor 110 to analyze the pathological slide image is the same as described above with reference to operation 310.

Then, the processor 110 performs a second classification on the plurality of cells expressed in the pathological slide image. In an embodiment, the processor 110 classifies the cells expressed in the pathological slide image into at least one of a tumor cell, a lymphocyte cell, and other cells. However, the example in which the processor 110 classifies the cells expressed in the pathological slide image is not limited thereto. In other words, the processor 110 may group the cells expressed in the pathological slide image according to various criteria for classifying different types of cells.

Hereinafter, an example in which the processor 110 performs a second classification on a plurality of cells will be described with reference to FIG. 5.

Figure 5:
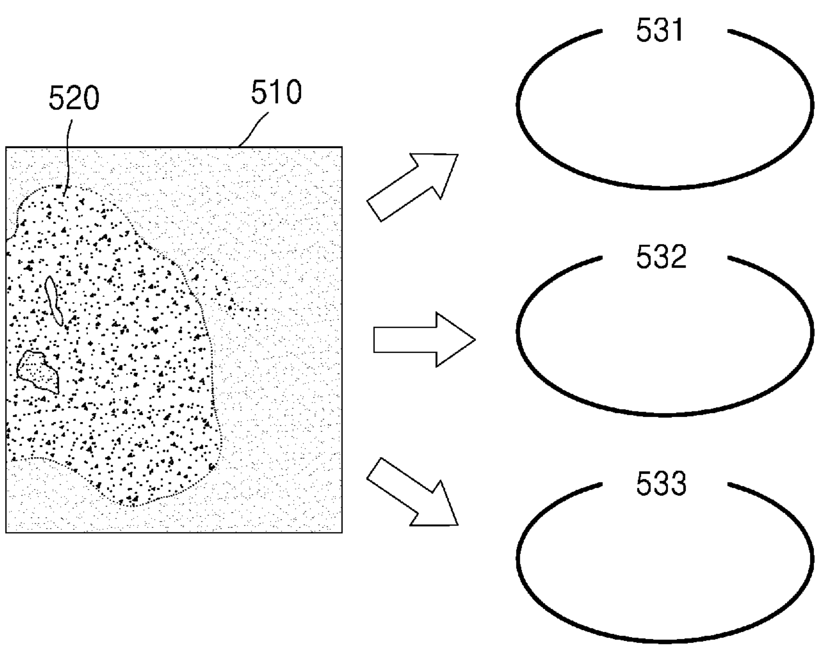
FIG. 5 shows a diagram for describing an embodiment in which a processor performs a second classification on a plurality of cells according to an embodiment.

FIG. 5 shows a diagram for describing an embodiment in which a processor performs a second classification on a plurality of cells according to an embodiment.

Referring to FIG. 5, the processor 110 analyzes a pathological slide image 510 to identify cells in a tissue 520. In an embodiment, the processor 110 detects a portion representing cells in the pathological slide image 510 and separates layers representing the cells.

The tissue 520 may include a plurality of cells, and the cells may include various types of cells. The processor 110 classifies cells into at least one of a tumor cell 531, a lymphocyte cell 532, and other cells 533. In this regard, the other cells 533 include normal cells. For example, the other cells 533 may include, but are not limited to, at least one of an epithelial cell, a nerve cell, a muscle cell, and a connective tissue cell.

Due to the classification of cells according to the described criteria by the processor 110, the classification results for areas of the tissue 520 may also be used for the calculation of the tumor purity.

Referring back to FIG. 3, in operation 330, the processor 110 combines the first classification result and the second classification result to calculate the tumor purity including information on noise included in the pathological slide image.

The processor 110 calculates the tumor purity by using the classification result for the tissue area and the classification result for the cells. As described above with reference to operations 310 and 320, since the processor 110 also identifies and classifies noise in the pathological slide image, information on noise may be included in the tumor purity calculation result.

The processor 110 may calculate the size of each area included in the tissue and the number of cells in each area through operations 310 and 320. In an embodiment, the processor 110 may calculate the size of the cancer area CA, the size of the cancer stroma area CS, the size of the necrosis area NC, the size of the degraded area DA, and the size of the background area BG. In an embodiment, the processor 110 may calculate the number of tumor cells $CA_t$ in the cancer area CA, the number of tumor cells $CS_t$ in the cancer stroma area CS, the number of tumor cells $NC_t$ in the necrosis area NC, the number of tumor cells $DA_t$ in the degraded area DA, and the number of tumor cells $BG_t$ in the background area BG. In an embodiment, the processor 110 may calculate the number of lymphocyte cells $CA_l$ in the cancer area CA, the number of lymphocyte cells $CS_l$ in the cancer stroma area CS, the number of lymphocyte cells $NC_l$ in the necrosis area NC, the number of lymphocyte cells $DA_l$ in the degraded area DA, and the number of lymphocyte cells $BG_l$ in the background area BG. In an embodiment, the processor 110 may calculate the number of other cells $CA_b$ in the cancer area CA, the number of other cells $CS_b$ in the cancer stroma area CS, the number of other cells $NC_b$ in the necrosis area NC, the number of other cells $DA_b$ in the degraded area DA, and the number of other cells $BG_b$ in the background area BG.

In an embodiment, the processor 110 may calculate a ratio of the number of tumor cells included in the cancer area with respect to the total number of cells included in the pathological slide image. For example, the processor 110 may calculate the ratio AI−P according to Equation 1.

$$AI-P\ (\%) = \frac{CA_t}{CA_t + CS_t + BG_t + CA_l + CS_l + BG_l + CA_b + CS_b + BG_b} * 100 \quad \text{[Equation 1]}$$

Referring to Equation 1, the processor 110 may calculate a first value AI–P for tumor purity by using the number of tumor cells $CA_t$, $CS_t$, and $BG_t$, the number of lymphocyte cells $CA_l$, $CS_l$, and $BG_l$, and the number of other cells $CA_b$, $CS_b$, and $BG_b$, included in the cancer area CA, the cancer stroma area CS, and the background area BG.

In an embodiment, the processor 110 may calculate a ratio of the cancer area to the entire area included in the pathological slide image. For example, the processor 110 may calculate the ratio CEA described above according to Equation 2 below.

$$CEA\ (\%) = \frac{CA}{CA + CS + BG} * 100 \quad \text{[Equation 2]}$$

Referring to Equation 2, the processor 110 may calculate a second value CEA for the tumor purity by using the size of the cancer area CA, the size of the cancer stroma area CS, and the size of the background area BG.

Also, the processor 110 may calculate various values related to biological noise. In an embodiment, the processor 110 may calculate the ratio of the non-cancer area (i.e., the normal area), the ratio of the necrosis area, and the ratio of the expected biological noise in the cancer area. Herein, the ratio of the non-cancer area (that is, the normal area) refers to the ratio of the area of the background area to the total area, the ratio of the necrosis area refers to the ratio of the necrosis area to the total area, and the ratio of the expected biological noise in the cancer area refers to the ratio of the number of other cells in the cancer area to the total number of cells.

For example, the processor 110 may calculate various values related to biological noise according to Equations 3 to 5 below.

$$\text{Non-cancer region}\ (\%) = \frac{BG}{CA + CS + BG} * 100 \quad \text{[Equation 3]}$$

Referring to Equation 3, the processor 110 may calculate a non-cancer area (that is, the normal area) by using the size of the cancer area CA, the size of the cancer stroma area CS, and the size of the background area BG.

$$\text{Necroptosis}\ (\%) = \frac{NC}{CA + CS + BG} * 100 \quad \text{[Equation 4]}$$

Referring to Equation 4, the processor 110 may calculate the ratio of the necrosis area by using the size of the cancer area CA, the size of the cancer stroma area CS, the size of the background area BG, and the necrosis area NC.

$$\text{Expected biological noise from cancer area}\ (\%) = \frac{CA_b}{CA_t + CS_t + BG_t + CA_l + CS_l + BG_l + CA_b + CS_b + BG_b} * 100 \quad \text{[Equation 5]}$$

Referring to Equation 5, the processor 110 may calculate the ratio of the expected biological noise in the cancer area by using the number of tumor cells $CA_t$, $CS_t$, and $BG_t$, the number of lymphocyte cells $CA_l$, $CS_l$, and $BG_l$, and the number of other cells $CA_b$, $CS_b$, and $BG_b$, included in the cancer area CA, the cancer stroma area CS, and the background area BG.

In an embodiment, the processor 110 may calculate a value related to technical noise. In this regard, the value related to the technical noise includes a ratio of the size of the degraded area to the size of the total area. For example, the processor 110 may calculate a value related to technical noise according to Equation 6 below.

$$\text{Technical noise}\ (\%) = \frac{DA}{CA + CS + BG} * 100 \quad \text{[Equation 6]}$$

Referring to Equation 6, the processor 110 may calculate the value related to technical noise by using the size of the cancer area CA, the size of the cancer stroma area CS, the size of the background area BG, and the size of the degraded area DA.

The various pieces of information on the tumor purity described above with reference to Equations 1 to 6 helps the user 30 to accurately diagnose a disease or to accurately determine the need for additional experiments. In other words, the processor 110 according to an embodiment may provide accurate information to the user 30 compared to the prior art by calculating the tumor purity in consideration of information corresponding to noise in the pathological slide image 410.

Figure 6:
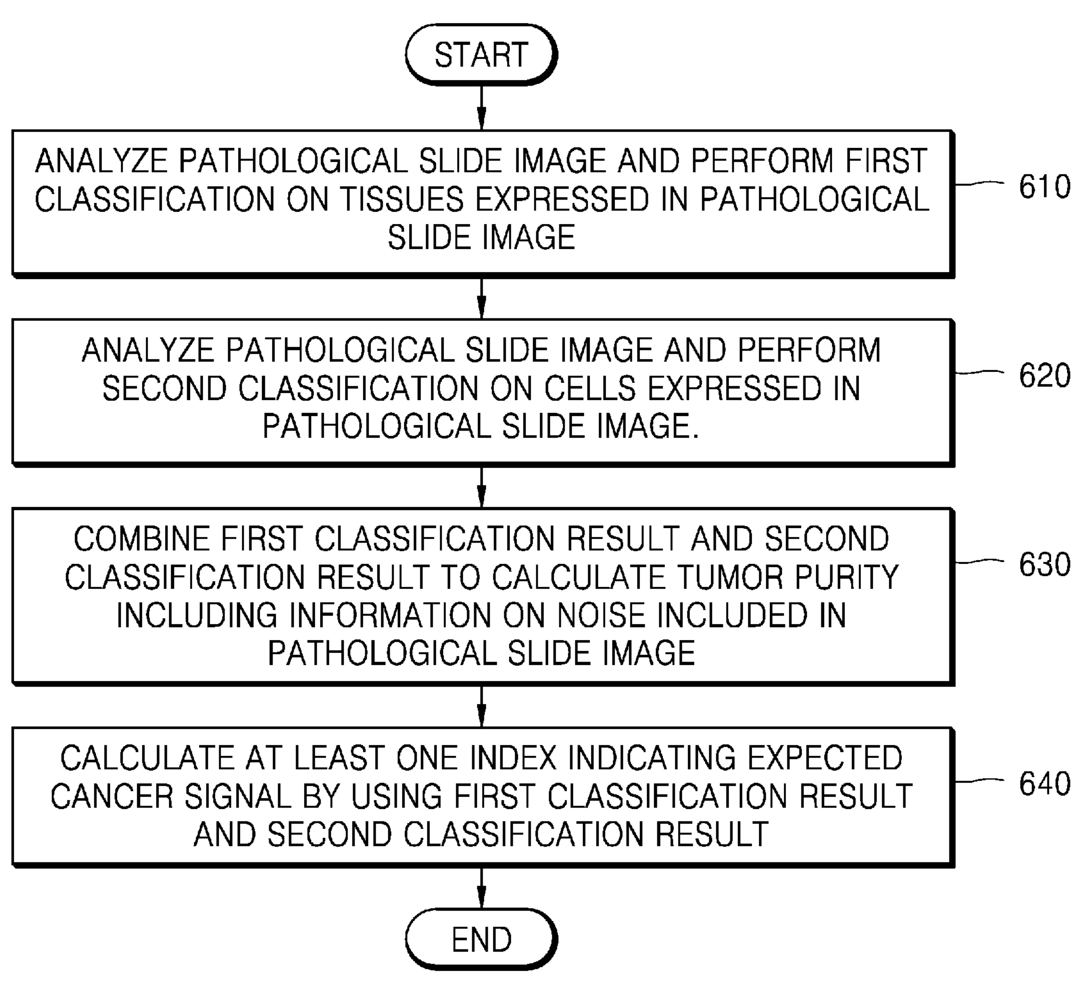
FIG. 6 shows a flowchart illustrating an example of a method of interpreting a pathological slide image according to an embodiment.

FIG. 6 shows a flowchart illustrating an example of a method of interpreting a pathological slide image according to an embodiment.

Referring to FIG. 6, operations 610 to 630 correspond to operations 310 to 330 of FIG. 3. Accordingly, detailed descriptions of operations 610 to 630 are omitted below.

In operation 640, the processor 110 calculates at least one index indicating an expected cancer signal by using the first classification result and the second classification result.

As described above with reference to operations 310 and 320 of FIG. 3, the processor 110 may calculate the size of each area included in the tissue and the number of cells in each area. The processor 110 may calculate an index indicating an expected cancer signal by using the number of cells in each area.

In an embodiment, the processor 110 may calculate an expected DNA yield with respect to all cells. In an embodiment, the processor 110 may calculate the molecular weight corresponding to the pathological slide image by using the total number of cells included in the pathological slide image. For example, the processor 110 multiplies the DNA weight of a single cell (e.g., 6 picograms (pg)) by the total number of cells, and converts the obtained value to nanograms (ng) with respect to the total amount of DNA to calculate the expected DNA yield with respect to total cells.

In an embodiment, the processor 110 may calculate an expected tumor DNA yield with respect to tumor cells. In an embodiment, the processor 110 may multiply the number of total tumor cells included in the pathology slide by the DNA weight of a single cell, and convert the obtained result to nanograms (ng) to calculate the expected tumor DNA yield with respect to the tumor cells.

Meanwhile, when the expected tumor DNA yield for tumor cells is divided by the expected DNA yield for all cells, the first value AI-P for the tumor purity described above with reference to Equation 1 may also be derived.

The expected cancer signal may be estimated according to how much volume the user 30 eluted during the nucleic acid isolation process. For example, when the user 30 isolates DNA with a total volume of 50 μL elution buffer, the ratio of tumor signal is diluted by dividing the first value AI-P for tumor purity by 49 (1:49). In the case of an expected cancer signal of less than a specific percentage, it may serve as a basis for providing a guide to the user 30 on whether to perform an additional experiment. An example in which the processor 110 provides a guide to the user will be described later with reference to FIGS. 9 and 10.

Figure 7:
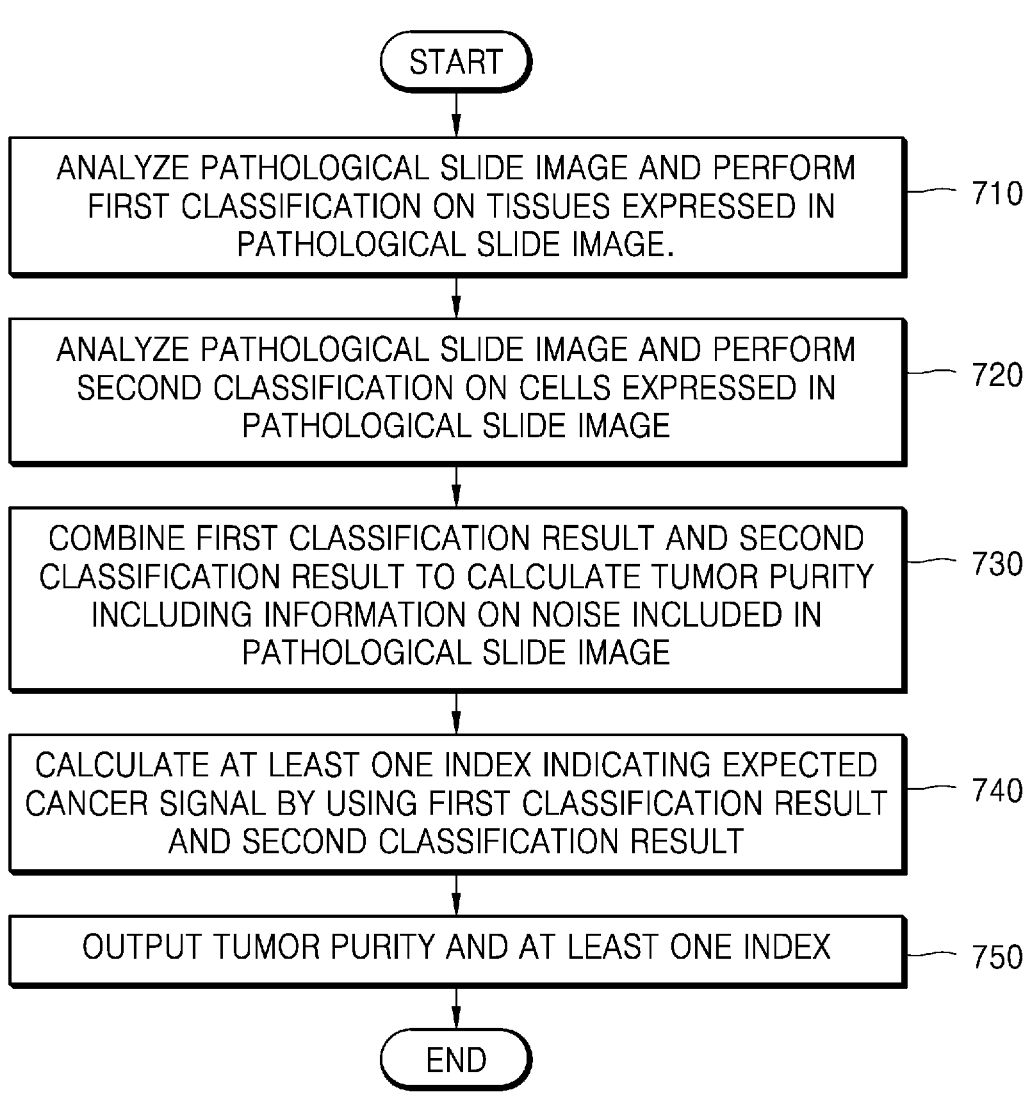
FIG. 7 shows a flowchart illustrating an example of a method of interpreting a pathological slide image according to an embodiment.

FIG. 7 shows a flowchart illustrating an example of a method of interpreting a pathological slide image according to an embodiment.

Referring to FIG. 7, operations 710 to 740 correspond to operations 610 to 640 of FIG. 6. Accordingly, detailed descriptions of operations 710 to 740 are omitted below.

In operation 750, the processor 110 outputs the tumor purity and at least one index. For example, the processor 110 may be configured to control a display device to output the calculation values described above with reference to FIGS. 3 to 6 and/or medical information obtained based on the calculation values.

Also, although not shown in FIG. 7, the processor 110 may be configured to control the communication module 140 to transmit the calculation values and/or medical information obtained based on the calculation values to a server or other external device. In an embodiment, the processor 110 may be configured to store the calculation values and/or the medical information obtained based on the calculation values in the memory 120.

FIG. 8 shows a view for describing an example in which tumor purity and at least one index are output according to an embodiment.

Referring to FIG. 8, the processor 110 may be configured to control the display device in such a way that values 810 indicating the tumor purity described above with reference to FIGS. 3 to 5 and values 820 related to the index described above with reference to FIG. 6 are output.

Accordingly, the user 30 may identify various pieces of information included in the pathological slide image, in particular, information classified as noise. Accordingly, a user 30 may identify accurate information on tumor purity for tissues and cells expressed in the pathological slide image. In addition, the user 30 may determine whether to perform an additional experiment to diagnose the disease.

Figure 9:
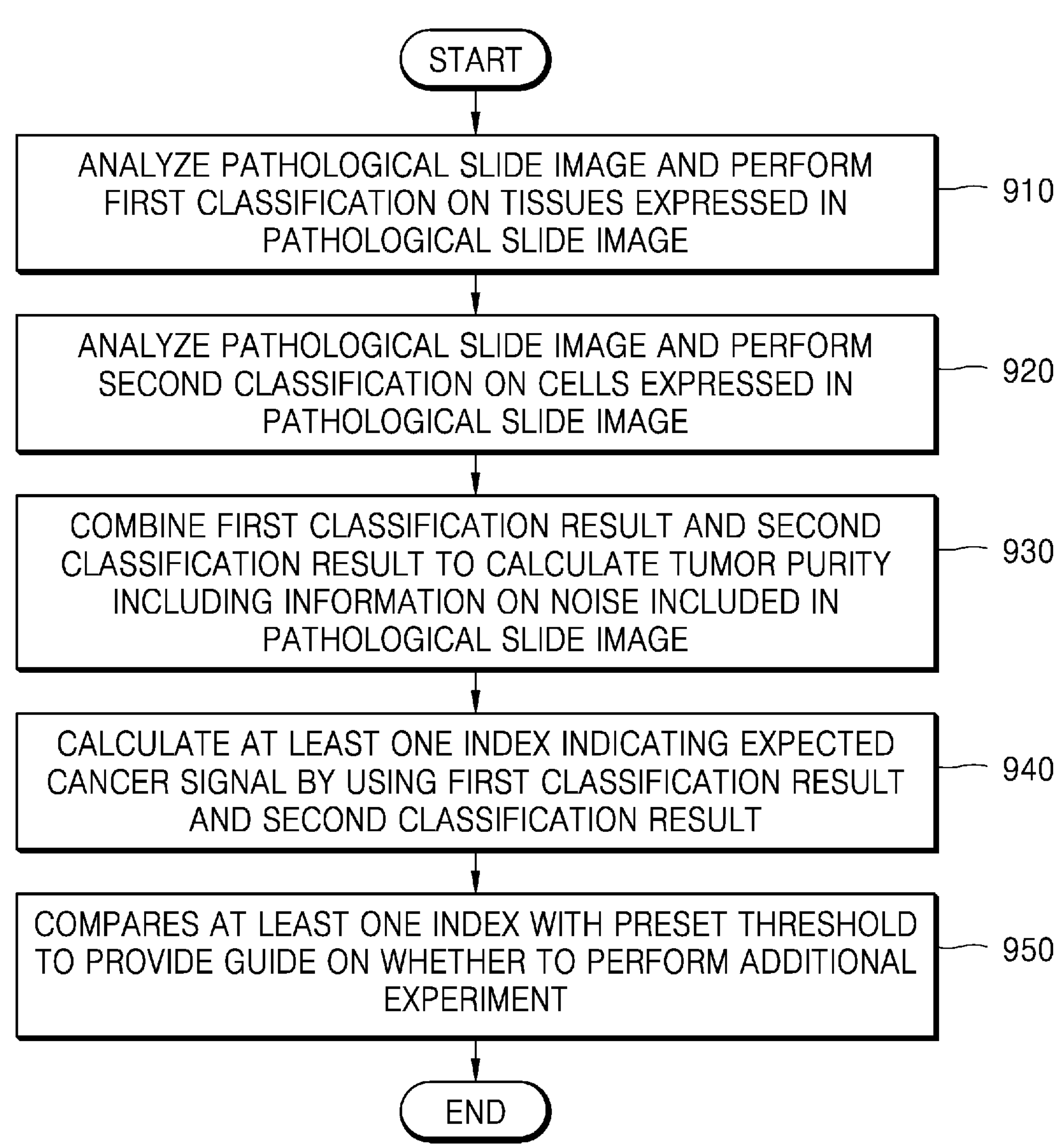
FIG. 9 shows a flowchart illustrating an example of a method of interpreting a pathological slide image according to an embodiment.

FIG. 9 shows a flowchart illustrating an example of a method of interpreting a pathological slide image according to an embodiment.

Referring to FIG. 9, operations 910 to 940 correspond to operations 610 to 640 of FIG. 6. Accordingly, detailed descriptions of operations 910 to 940 are omitted below.

In operation 950, the processor 110 compares at least one index with a preset threshold to provide a guide on whether to perform an additional experiment.

As described above with reference to operation 640 of FIG. 6, the processor 110 may estimate the expected cancer signal according to how much volume the user 30 eluted during the nucleic acid separation process.

In an embodiment, the expected cancer signal below a certain percentage may have to be classified as 'no-go' for quantitative PCR (qPCR) or other experiments below the detection limit according to the preset threshold. Here, the preset threshold may be set by user 30, and the set value may be adjustable.

For example, it is assumed that the user 30 designs an experiment with quantitative PCR (qPCR) and the threshold is set to be 1%. In the case where when the amount of input DNA is 47 μL, the expected cancer signal can be 1% or more, an experiment in which the amount of DNA input is less than 47 μL, should be classified as 'no-go'.

Since the processor 110 compares the expected cancer signal with the threshold and provides a guide on whether to perform an additional experiment, the user 30 may easily design a threshold that can be detected with a single slide.

Figure 10:
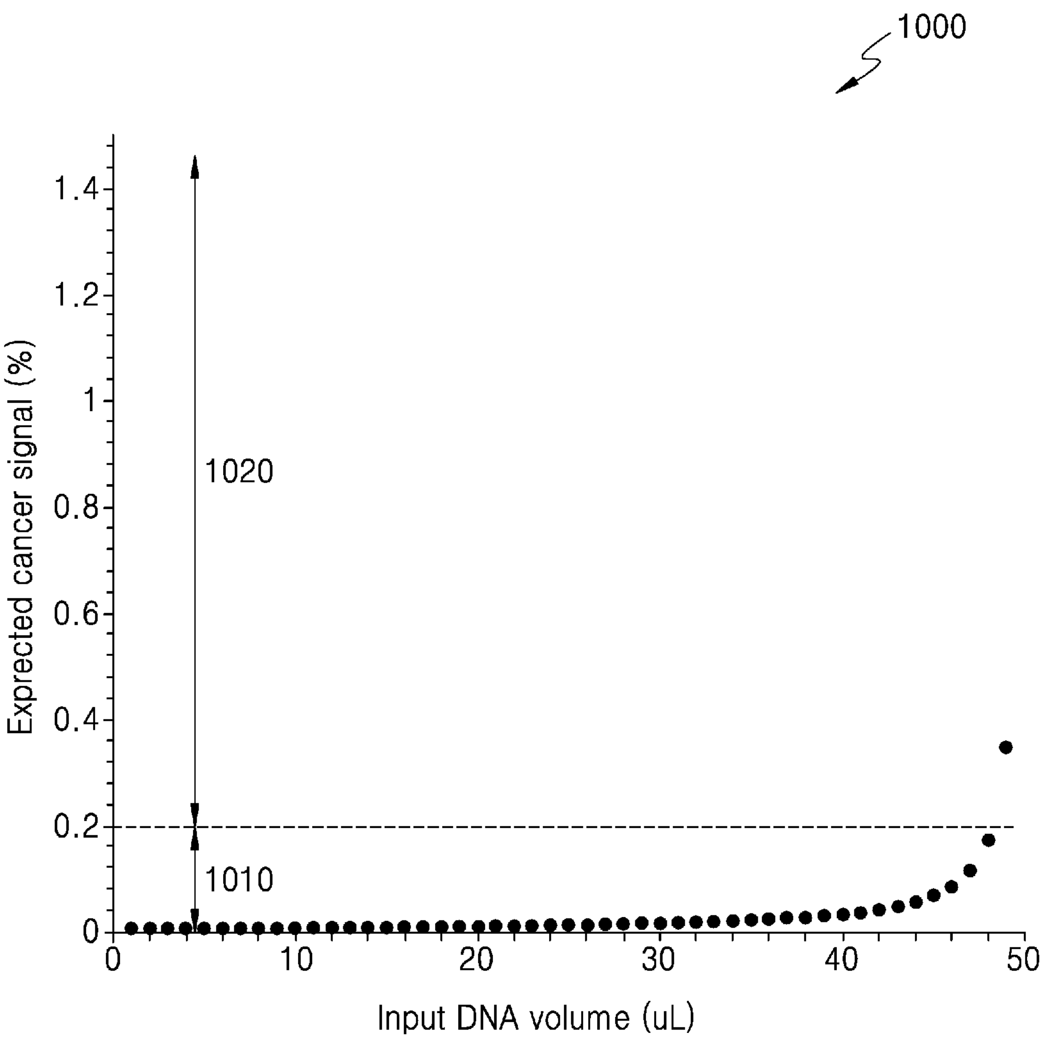
FIG. 10 shows a diagram for describing an example of a guide provided by a processor according to an embodiment.

FIG. 10 shows a diagram for describing an example of a guide provided by a processor according to an embodiment.

Referring to FIG. 10, the processor 110 may generate a graph representing an expected cancer signal with respect to an input amount of DNA. However, the guide generated by the processor 110 is not limited to the graph shown in FIG. 10, and various other types of guides (e.g., a table, etc.) may be used.

For example, assuming that an expected cancer signal of 0.2% is set as the threshold, the processor 110 may separately output values 1010 with an expected cancer signal of less than 0.2% and values 1020 with an expected cancer signal of 0.2% or more. Accordingly, the user 30 may determine whether to perform an additional experiment by examining the output guide.

Figure 11:
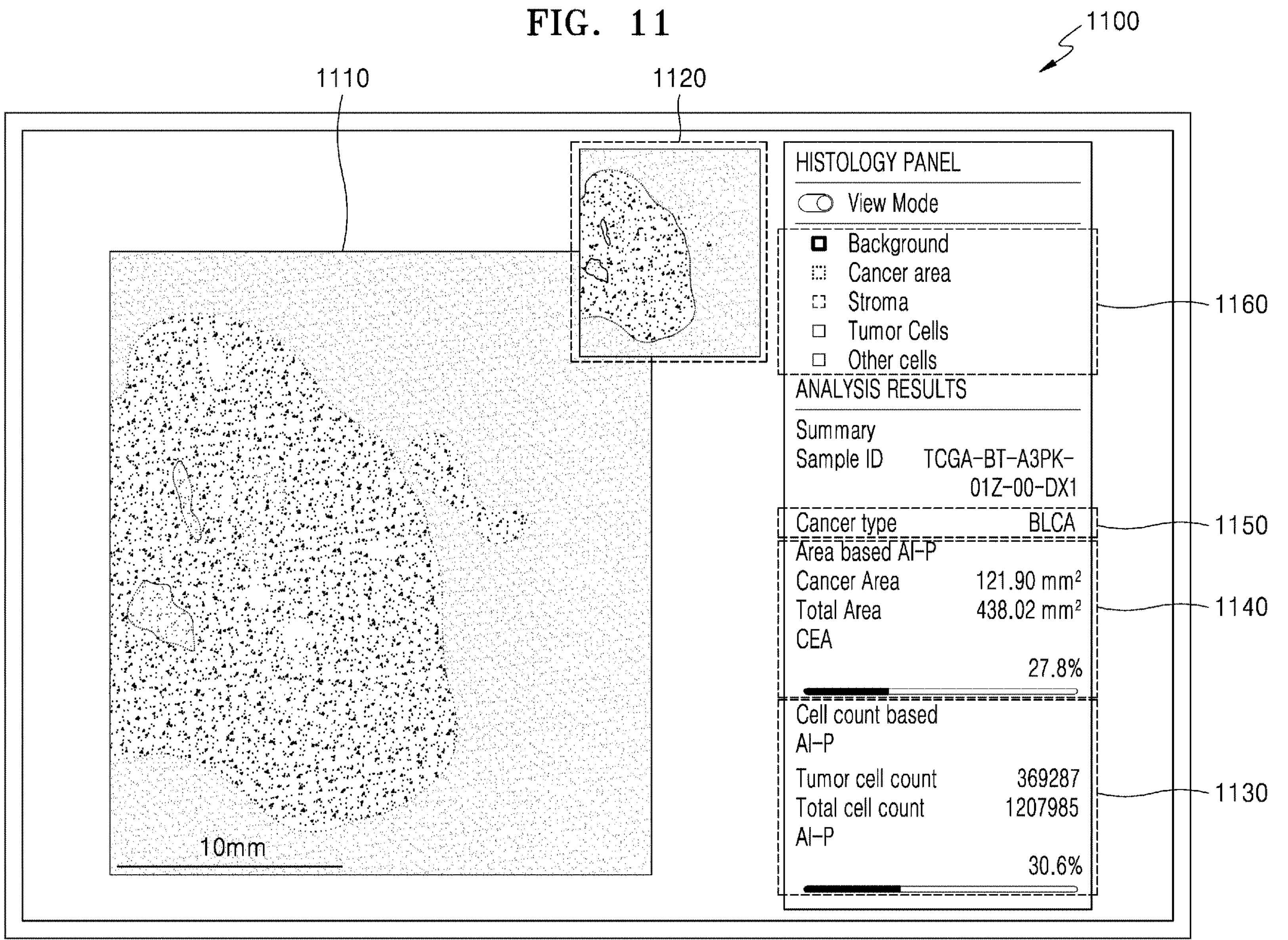
FIG. 11 shows a diagram illustrating an example in which a pathological slide image and various pieces of information are output according to an embodiment.

FIG. 11 shows a diagram illustrating an example in which a pathological slide image and various pieces of information are output according to an embodiment.

FIG. 11 shows an example of an image 1100 output on a display device. For example, the image 1100 may include a pathological slide image 1110 and a thumbnail image 1120. The pathological slide image 1110 may be enlarged or reduced according to the manipulation by the user 30. In the thumbnail image 1120, an area that is observed by the user 30 and an area that is not observed by the user 30 may be separately displayed. Also, an area of interest that needs to be observed by the user 30 may be displayed in the thumbnail image 1120.

Also, the image 1100 may include various pieces of information 1130, 1140, and 1150 according to the interpretation of the pathological slide image 1100. In an embodiment, the image 1100 may include the various calculation values 1130 and 1140 described above with reference to FIGS. 3 to 10, and the type of cancer 1150 corresponding to the pathological slide image 1100 may also be included.

In addition, the image 1100 may include an area 1160 in which cells and areas classified according to the interpretation of the pathological slide image 1100 can be selected. By selecting some or all of the output on the area 1160, the user 30 may perform an observation on only a target object in the pathological slide image 1100.

As described above, the processor 110 may calculate the tumor purity including information on noise included in the pathological slide image. Accordingly, a user 30 may identify accurate information on tumor purity for tissues and cells expressed in the pathological slide image.

In an embodiment, the processor 110 may calculate the tumor purity using an AI model trained to predict 32 types of tumor samples from The Cancer Genome Atlas (TCGA). Accordingly, the user 30 may accurately diagnose all types of cancer.

The processor 110 may calculate an index indicating an expected cancer signal. Accordingly, the user 30 may determine whether to perform an additional experiment to diagnose the disease.

Meanwhile, the method described above may be written as a program that can be executed on a computer, and can be implemented in a general-purpose digital computer that operates the program using a computer-readable recording medium. In addition, the structure of the data used in the above-described method may be recorded on a computer-readable recording medium through various manners. The computer-readable recording medium includes a storage medium such as a magnetic storage medium (e.g., ROM, RAM, USB, floppy disk, hard disk, etc.) and an optically readable medium (e.g., CD-ROM, DVD, etc.).

A person of ordinary skill in the art related to this embodiment would understand that it can be implemented in modified forms without departing from the essential characteristics of the description provided above. Therefore, the disclosed methods should be considered in an illustrative aspect rather than a restrictive aspect, and the scope of the rights is indicated in the claims rather than the foregoing description, and should be construed to include all differences within the scope equivalent thereto.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A computing apparatus comprising:

memory storing instructions; and at least one processor, wherein the instructions cause the at least one processor to:

perform a first classification on a plurality of tissues expressed in a pathological slide image by analyzing the pathological slide image;

perform a second classification on a plurality of cells expressed in the pathological slide image by analyzing the pathological slide image;

classify tumor cells among cells included in a cancer area in the pathological slide image by combining the first classification result and the second classification result;

determine a total number of cells corresponding to a number of the tumor cells, a number of lymphocyte cells, and a number of other cells included in the cancer area, a cancer stroma area, and a background area in the pathological slide image, wherein the background area includes an area representing biological noise; and calculate tumor purity including information about a first ratio of the number of the tumor cells included in the cancer area with respect to the total number of cells, and information on technical noise included in the pathological slide image, wherein the information on the technical noise is calculated based on a size of a degraded area included in the pathological slide image.

2. The computing apparatus of claim 1, wherein the instructions further cause the at least one processor to perform the first classification by classifying the pathological slide image into the cancer area and at least one of the cancer stroma area, a necrosis area, or the background area.

3. The computing apparatus of claim 2, wherein the instructions further cause the at least one processor to calculate a second ratio of the cancer area with respect to the total area included in the pathological slide image by combining the first classification result and the second classification result.

4. The computing apparatus of claim 1, wherein the instructions further cause the at least one processor to perform the second classification by classifying the plurality of cells expressed in the pathological slide image into the tumor cells and at least one of a lymphocyte cell, or other cells.

5. The computing apparatus of claim 1, wherein the instructions further cause the at least one processor to calculate at least one index representing an expected cancer signal by using the first classification result and the second classification result.

6. The computing apparatus of claim 5, wherein the instructions further cause the at least one processor to control a display device to output the tumor purity and the at least one index.

7. The computing apparatus of claim 5, wherein the instructions further cause the at least one processor to provide a guide on whether to perform an additional experiment by comparing the at least one index with a preset threshold.

8. The computing apparatus of claim 1, wherein the instructions further cause the at least one processor to calculate at least one of an expected DNA yield for all cells and an expected tumor DNA yield for tumor cells using the calculated tumor purity.

9. The computing apparatus of claim 1, wherein the information on the technical noise comprises a second ratio of the size of the degraded area to a size of a total area included in the pathological slide image comprising a size of the cancer area, a size of the cancer stroma area, and a size of the background area.

10. A method of interpreting a pathological slide image, the method comprising:

performing a first classification on a plurality of tissues expressed in the pathological slide image by analyzing the pathological slide image;

performing a second classification on a plurality of cells expressed in the pathological slide image by analyzing the pathological slide image; and classifying tumor cells among cells included in a cancer area in the pathological slide image by combining the first classification result and the second classification result;

determine a total number of cells corresponding to a number of the tumor cells, a number of lymphocyte cells, and a number of other cells included in the cancer area, a cancer stroma area, and a background area in the pathological slide image, wherein the background area includes an area representing biological noise; and calculating tumor purity including information about a first ratio of the number of the tumor cells included in the cancer area with respect to the total number of cells, and information on technical noise included in the pathological slide image, wherein the information on the technical noise is calculated based on a size of a degraded area included in the pathological slide image.

11. The method of claim 10, wherein the performing the first classification comprises classifying the pathological slide image into the cancer area and at least one of the cancer stroma area, a necrosis area, or the background area.

12. The method of claim 11, wherein the calculating the tumor purity comprises calculating a second ratio of the cancer area with respect to the total area included in the pathological slide image by combining the first classification result and the second classification result.

13. The method of claim 10, wherein the performing the second classification comprises classifying the plurality of cells expressed in the pathological slide image into the tumor cells and at least one of a lymphocyte cell, or other cells.

14. The method of claim 10, further comprising:

calculating at least one index representing an expected cancer signal by using the first classification result and the second classification result.

15. The method of claim 14, wherein the calculating the at least one index comprises calculating at least one of an expected DNA yield for all cells and an expected tumor DNA yield for tumor cells using the calculated tumor purity.

16. The method of claim 14, further comprising outputting the tumor purity and the at least one index.

17. The method of claim 14, further comprising providing a guide on whether to perform an additional experiment by comparing the at least one index with a preset threshold.

18. A non-transitory computer-readable recording medium having recorded thereon a program for executing the method of claim 10 in a computer.

* * * * *